United States Patent [19]

Bradshaw et al.

[11] Patent Number: 5,643,171

[45] Date of Patent: Jul. 1, 1997

[54] METHOD AND APPARATUS FOR UNIFORM RADIATION TREATMENT OF VASCULAR LUMENS

[75] Inventors: Anthony J. Bradshaw, Missouri City; Albert E. Raizner, Houston, both of Tex.

[73] Assignee: NeoCardia, LLC, Houston, Tex.

[21] Appl. No.: 339,950

[22] Filed: Nov. 15, 1994

Related U.S. Application Data

[63] Continuation-in-part of Ser. No. 57,322, May 4, 1993.

[51] Int. Cl.⁶ ..................................................... A61N 5/00
[52] U.S. Cl. ......................................... 600/1; 600/3
[58] Field of Search .......................... 600/1–8; 128/772; 606/191, 194, 195; 604/96–101

[56] References Cited

U.S. PATENT DOCUMENTS

| | | | |
|---|---|---|---|
| 4,815,449 | 3/1989 | Horowitz | 600/7 |
| 4,861,520 | 8/1989 | van't Hooft et al. | 252/644 |
| 5,059,166 | 10/1991 | Fischell et al. | 600/3 |
| 5,213,561 | 5/1993 | Weinstein et al. | 600/7 |
| 5,295,995 | 3/1994 | Kleiman | 606/194 |
| 5,302,168 | 4/1994 | Hess | 600/3 |
| 5,308,356 | 5/1994 | Blackshear, Jr. et al. | 606/194 |

FOREIGN PATENT DOCUMENTS

9102312 U  2/1991  Germany.

OTHER PUBLICATIONS

Weshler, et al., *Inhibition by irradiation of smooth muscle cell proliferation in the de-endothelialized rat aorta;* Oct. 1988; pp. 133–138.

Bottcher, et al.; *Endovascular Irradiation—A New Method to Avoid Recurrent Stenosis after Stent Implantation in Peripheral Arteries; Technique and Preliminary Results;* Nov. 1992; pp. 183–186.

Friedman, et al; *The Antiatherogenic Effect of Iridium 192 upon the Cholesterol-fed Rabbit;* pp. 185–192.

Friedman, et al; *Effect of Iridium 192 on Thromboatherosclerotic Plaque in the Rabbit Aorta;* pp. 285–290.

*Primary Examiner*—Angela D. Sykes
*Assistant Examiner*—John P. Lacyk
*Attorney, Agent, or Firm*—Wigman, Cohen, Leitner & Myers, P.C.

[57] ABSTRACT

A method and apparatus for intravascular radiotherapy for prevention of stenosis following angioplasty or other trauma to coronary arteries caused by smooth muscle cell hyperplasia in which a uniform dosage of radiation is delivered to the walls of the artery by positively positioning a radioactive source at the radial center of the artery being treated.

24 Claims, 4 Drawing Sheets

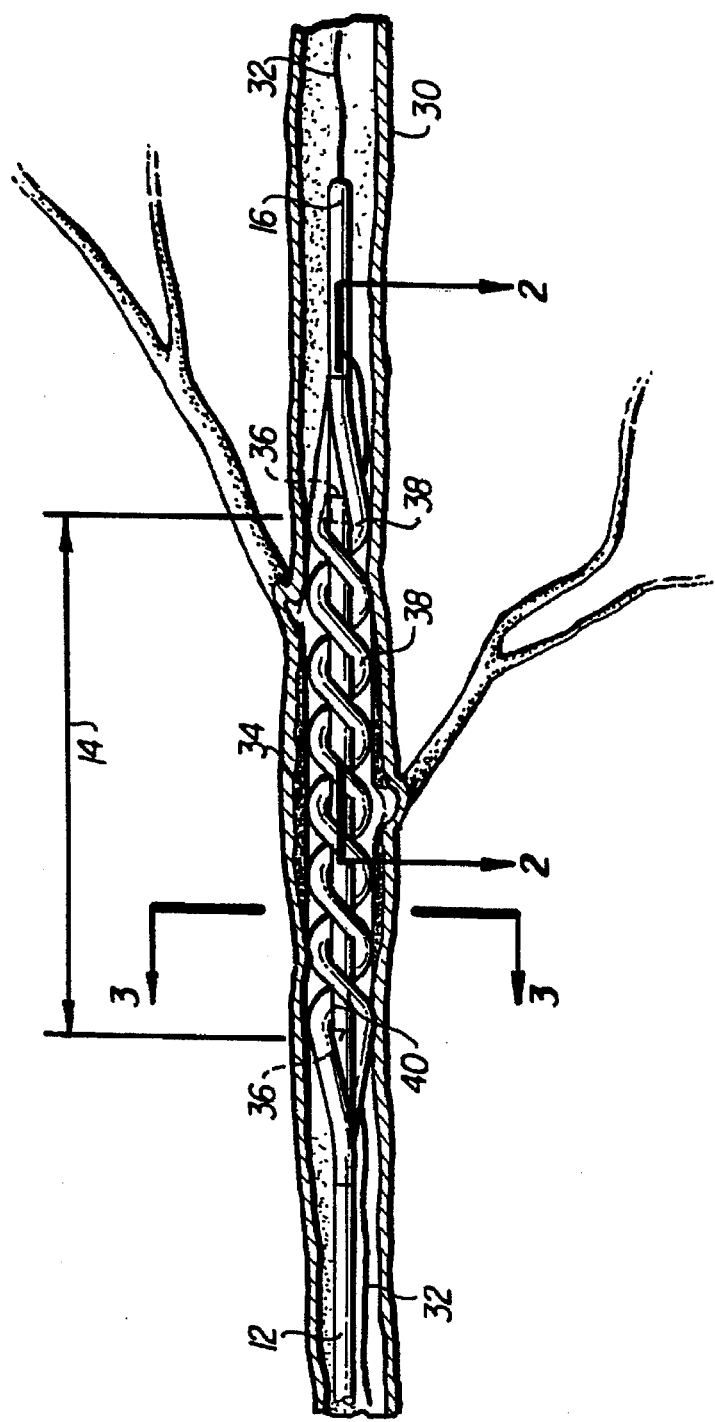
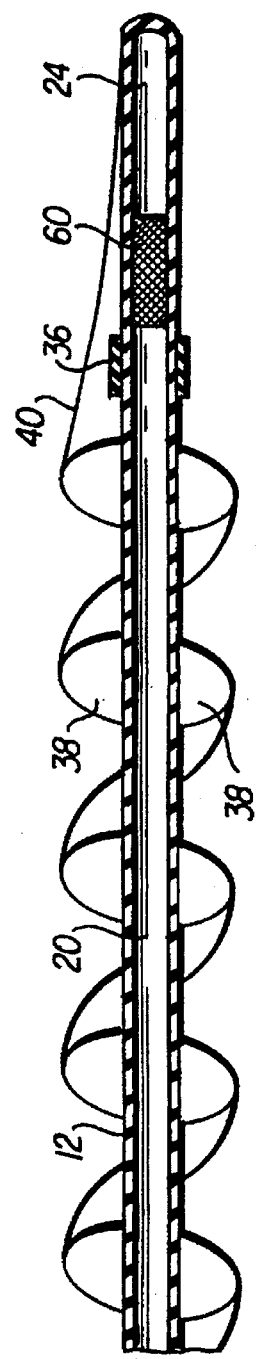

METHOD AND APPARATUS FOR UNIFORM RADIATION TREATMENT OF VASCULAR LUMENS

CROSS-REFERENCE TO RELATED APPLICATION

This application is a continuation-in-part of co-pending application of A. J. Bradshaw, Ser. No. 08/057,322, filed May 4, 1993, pending.

BACKGROUND OF THE INVENTION

This invention relates generally to treatment of selected tissue by inter-vivo radiation, specifically to radiation treatment of selected regions of the cardiovascular system that have been subjected to trauma to prevent restenosis of the traumatized region, more specifically to radiation treatment to prevent restenosis of an artery traumatized by percutaneous transluminal angioplasty (PTA).

PTA treatment of the coronary arteries, percutaneous transluminal coronary angioplasty (PTCA), also known as balloon angioplasty, is the predominant treatment for coronary vessel stenosis. Approximately 300,000 procedures were performed in the United States (U.S.) in 1990 and an estimated 400,000 in 1992. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% of all patients requiring repeat PTCA procedures or by-pass surgery, with attendant high cost and added patient risk. More recent attempts to prevent restenosis by use of drugs, mechanical devices, and other experimental procedures have had limited success.

Restenosis occurs as a result of injury to the arterial wall during the lumen opening angioplasty procedure. In some patients, the injury initiates a repair response that is characterized by hyperplastic growth of the vascular smooth muscle cells in the region traumatized by the angioplasty. The hyperplasia of smooth muscle cells narrows the lumen that was opened by the angioplasty, thereby necessitating a repeat PTCA or other procedure to alleviate the restenosis.

Preliminary studies indicate that intravascular radiotherapy (IRT) has promise in the prevention or long-term control of restenosis following angioplasty. It is also speculated that IRT may be used to prevent stenosis following cardiovascular graft procedures or other trauma to the vessel wall. A proposed IRT method is first to advance a flexible catheter (radioguide catheter) through the cardiovascular system of the patient until the distal tip is at or near the region of the vessel that has been subjected to the angioplasty procedure. Subsequently, a treatment catheter, comprising a wire or small catheter having a radiation source at the tip (hereinafter referred to as a source wire), is advanced through the radioguide catheter until the radiation source is disposed at the affected region. The radiation source is held at the affected region for a predetermined treatment period calculated to deliver an effective dose of radiation, then is withdrawn.

A principal shortcoming in current IRT methods and apparatus, however, is the lack of any provision to control the radial location of the radioactive source within the lumen during treatment. The effective dose to inhibit smooth muscle cell hyperplasia and the resulting restenosis is approximately 1,000–3,000 rads. For a given source activity, the intensity of the radiation drops rapidly as a function of the distance from the source. Accordingly, if the source is not held reasonably near the center of the lumen, for a given treatment period, the portion of the vessel wall nearest the source will receive an excess dose of radiation, while the portion of the vessel wall farthest from the source will receive less than the prescribed dose. Overdosing of a section of blood vessel can cause arterial necrosis, inflammation and hemorrhaging. Underdosing will result in no inhibition of smooth muscle cell hyperplasia, or even exacerbation of the hyperplasia and resulting restenosis.

Current IRT methods do not provide for centering of the radiation source within the lumen to provide substantially uniform irradiation. U.S. Pat. No. 5,199,939 to Dake et al. teaches the use of a catheter having a radiation source assembled at the tip for treatment of vascular lumens to prevent restenosis. This patent does not, however, teach centering to provide uniform irradiation of the walls of the vessel during treatment.

U.S. Pat. No. 5,302,168 to Hess also discloses use of a radioactive source positioned within the stenosed region of an artery to inhibit restenosis. This patent, however, does not address non-uniform irradiation as a potential problem, nor does it teach centering to provide uniform irradiation.

U.S. Pat. No. 5,213,561 to Weinstein et al. also does not address non-uniform irradiation as a potential problem and does not teach centering of the radioactive source as a method of providing uniform irradiation. In one embodiment, the radioactive material is placed on a catheter tube inside the balloon of a balloon catheter, with a retractable radiation shield surrounding the source so that the shield may be retracted to expose the source immediately following completion of angioplasty. Although the balloon catheter of this embodiment has an internal tube, the tube is not constrained to be positioned at the center of the balloon. Moreover, the patent does not contain a teaching of centering the radioactive material. In fact, the relevant disclosed embodiment shows the radioactive crystals mounted eccentrically on the tube.

H. Böttcher, et al. of the Johann Wolfgang Goerhe University Medical Center, Frankfurt, Germany reported in November 1992 of having treated human superficial femoral arteries with a calculated dose of 12 Gray (1,200 rads) from a 10 Curie source. Böttcher, et al. recognized that the theoretical dosage from a fixed radiation source within the vessel varied with distance from the source. However, Böttcher, et al. do not teach centering as a means to prevent inconsistent irradiation of the vessel walls as a result of distance variations. Instead, Böttcher, et al. teach that the dynamic process of the catheter floating in the relatively straight femoral artery lumen mitigates the tissue damage anticipated from the inconsistent irradiation.

Accordingly, it is a principal object of the present invention to provide a method and apparatus for intravascular radiotherapy in which a uniform dose of radiation is delivered to the wall of the blood vessel by centering the radioactive source within the lumen. A further object of the present invention is to provide for a compliant centering means that will conform to the tortuous curves in and around the coronary arteries while maintaining the radioactive source at the center of the artery for the entire length of the region being treated.

Because current IRT methods and apparatus do not provide for centering the radiation source within the lumen, they also do not address centering the radiation source without obstructing the flow of blood through the blood vessel being treated. Obstruction of a coronary artery for a prolonged period of type, typically for more than approximately one minute may cause impairment of heart function or irritability of the heart and may result in suffer severe ischemia, angina, cardiac arrest, myocardial infarction (a heart attack), and/or shock. The radiation sources used for IRT are preferably of relatively small mass and size. Typically, to deliver an effective dose, these sources must remain centered in the target area for a minimum of approximately 4 minutes. Any means for centering the radiation source that blocked the flow of blood could only be used in a coronary artery for less than about one minute at a time, necessitating either multiple repeat irradiation treatments with intervening periods of perfusion, or use of a less preferable larger source.

Accordingly, another related object is to provide a radioactive source centering method and apparatus that allows per fusion of blood past the radiation source during the treatment period.

SUMMARY OF THE INVENTION

According to the present invention the IRT procedure is accomplished by providing for positive positioning of the radiation source substantially at the radial center of the vessel in the target area being treated and maintaining the position for the duration of the treatment, followed by removal of the radiation source from the patient. According to one feature of the invention, proper positioning of the radiation source is accomplished by selecting a hollow radioguide catheter that is appropriately sized for the particular vessel being treated. A longitudinal bore in the radioguide catheter comprises a treatment channel through which a radiation source may be advanced. The radioguide catheter also includes means for centering the distal end of the treatment channel within the vessel. The centering means may be a molded catheter tip, a wire form, or preferably a balloon. In use, the catheter is advanced through the cardiovascular system until the distal tip is disposed in the target area of the blood vessel to be treated, which may be a portion of an artery previously enlarged by angioplasty. A source wire comprising a flexible elongate member having a radiation source assembled at the distal tip is pushed through the treatment channel in the radioguide catheter until the radiation source is also disposed at the target area. By substantially centering the treatment channel within the blood vessel lumen, the radioactive source of the source wire, is substantially centered within the lumen.

According to a preferred embodiment of the invention, the centering is accomplished by means of a balloon attached to the distal portion of the radioguide catheter. When inflated, the balloon engages the walls of the vessel to center the treatment channel. The balloon is configured to center the treatment channel whether in straight or tortuous vessels. The balloon configuration may also have helical lobes, straight flutes, or other features on the exterior surface, which define a corresponding passageway between the balloon and the wall of the blood vessel to permit perfusion of blood when the balloon is inflated. The radioguide catheter also may have one or more longitudinal holes in addition to the treatment channel for passage of a guidewire and for balloon inflation.

BRIEF DESCRIPTION OF THE DRAWINGS

The above and other objects, aspects, features and attendant advantages of the present invention will become apparent from a consideration of the ensuing detailed description of presently preferred embodiments and methods thereof, taken in conjunction with the accompanying drawings, in which:

FIG. 1 is a segmented view of an embodiment of the present invention disposed in a blood vessel;

FIG. 2 is a partial longitudinal cross sectional view of the embodiment of FIG. 1 taken along line 2—2.

DESCRIPTION OF PREFERRED EMBODIMENTS AND METHODS

Figure 3A:
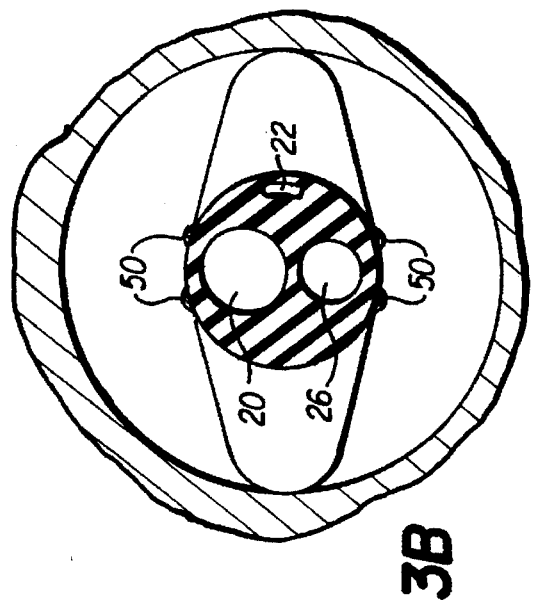
FIG. 3A is a transverse sectional view of the embodiment of FIG. 1 taken at line 3—3.

The present invention is directed to providing a method and apparatus for delivering a uniform dose of radiation to the walls of a blood vessel. Referring to FIGS. 1, 2 and 3A, FIG. 1 shows an embodiment of the present invention comprising a radioguide catheter 10 having cylindrical shaft 12 having distal treatment section 14 and distal tip 16. Attached to distal treatment section 14 of shaft 12 is centering balloon 40 having helical lobes 38. Radioguide catheter 10 is shown disposed in target area 34, which comprises the region of blood vessel 30 that has previously been subjected to an angioplasty procedure to relieve stenosis. FIG. 2 is a longitudinal cross section of the embodiment of FIG. 1 taken at line 2—2. FIG. 3A is a transverse cross section of the embodiment of FIG. 1 taken at line 3—3.

Referring to FIGS. 2 and 3A, shaft 12 comprises an elongate member having a treatment channel 20, balloon inflation lumen 22 and distal monorail guidewire lumen 24. As can be seen in FIGS. 1 and 2, distal monorail lumen 24 opens at the distal tip of shaft 12 and exits through the lateral surface of shaft 12 distal of balloon 40. Plug 60 is shown sealing guidewire lumen 24 from treatment channel 20, however, the two lumens could be formed separately. In use, guidewire 32 is positioned in blood vessel 30. Radioguide catheter 10 is then advanced over guidewire 32 with guidewire 32 exiting distal of balloon 40. Allowing guidewire 32 to exit the catheter distal of balloon 40 permits the minimum possible catheter diameter thereby facilitating introduction of the catheter into small arteries. Radioguide catheter 10 is advanced over guidewire 32 until treatment section 14 is disposed in the target area 34 of blood vessel 30.

Treatment channel 20 comprises a longitudinal bore in shaft 12 terminating proximate to distal tip 16 and may include teflon liner 28 to facilitate movement of a source wire longitudinally within the treatment channel. To simplify the geometry of balloon 40, treatment channel 20 may be cylindrical and centered about the axis of shaft 12, permitting lobes 38 to be of uniform height.

An important consideration in the design of radioguide catheter 10 is that the distal portion of treatment channel 20 be constrained to the center of the vessel within a fairly tight tolerance irrespective of the curvature of the region of the vessel being treated. For example, exposure to about 1,000 to 3,000 rads is believed to be a clinically effective treatment. Exposure levels above about 3,000 rads have been observed to cause arterial necrosis, inflammation, and hemorrhaging. Exposure levels below about 1,000 rads have been observed to be ineffective in preventing smooth muscle cell hyperplasia. The clinical effect of the radiation is dose sensitive. The more radiation the blood vessel absorbs, the greater the effect on inhibition of smooth muscle cell hyperplasia. Therefore the desired dose range for safe and effective clinical use is preferably about 1,500 to 2,500 rads.

To allow for a factor of safety, in use the radioactive source would be placed in the target area for a period of time calculated to deliver about 1,900 rads assuming perfect centering within the blood vessel. However, for a given source activity the intensity of the radiation falls off with the square of the distance from the source. Thus, small variations in the distance from the source to the blood vessel wall will rapidly bring the 1,900 rad theoretical exposure outside the 1,000 to 3,000 rad recommended range. For example, an $^{192}$Ir source is relatively tolerant of deviations from ideal conditions. However, if a coronary artery is opened to a 3 millimeter nominal diameter, an $^{192}$Ir source calculated to deliver 1,900 rads still must be centered to within 0.5 millimeter to deliver approximately 2,200 rads to the nearest point and 1,600 rads to the farthest point. If not centered, this nominal 1,900 rad dose delivered from an $^{192}$Ir source would deliver as much as 3,300 rads to the nearest point and as little as 750 rads to the farthest point of the same 3 millimeter lumen.

The energy absorption rate also varies from isotope to isotope with some types of isotopes having energy that is absorbed more quickly into tissue than others. Certain beta emitters have radiation that is absorbed very quickly into tissue. To achieve substantially uniform irradiation from such beta emitters, these sources must be centered even more precisely than an $^{192}$Ir source.

If the catheter shaft is attached to the centering balloon at the balloon endpoints only, although the balloon will conform to the curvature of the vessel, the catheter inside will tend to assume a straight configuration between the two attachment points. The greater the length of the balloon relative to its diameter, the more pronounced the deviation of the catheter from center will be. If the catheter shaft is attached to the balloon at regular intervals over the length of the balloon, the attachment points will tend to constrain the catheter to a piecewise linear approximation of the centerline of the vessel, and if the attachment points are continuous, the catheter will be continuously constrained to the centerline of the vessel. Preferably, therefore, balloon 40 is attached to shaft 12 by bonds 50, which are at regular intervals or are continuous over the length of the balloon.

For reliable centering, especially in curved blood vessels, the balloon 40 itself should be molded from a relatively non-compliant balloon material, such as polyvinyl chloride, polyelthyene, or polyethylene terephthalate, which will expand to a fixed diameter when inflated. Compliant materials such as latex could also be used, but would be much more sensitive to inflation pressure. In normal use, a catheter/balloon combination will be selected so that in its expanded state the balloon is just large enough to engage the walls of the blood vessel firmly. The balloon itself may be molded by any conventional means used for medical devices.

Bonds 50 may be thermal or ultrasonic welds, adhesive or solvent bonds, or other conventional means. Radio-opaque markers 36, which may be silver or other material commonly used for positioning catheters under fluoroscopy, are attached by conventional means to shaft 12 immediately outside or preferably immediately inside the limits of balloon 40 to mark the endpoints of treatment section 14 where inflated balloon 40 engages vessel 30. Alternately, markers 36 may be plated directly onto shaft 12 to minimize the volume dedicated to markers 36. In the distal monorail configuration, the distal marker 36 may be incorporated into plug 60 itself, which divides the distal monorail lumen 24 from treatment channel 20. Markers 36 are important to ensure not only that the distal section 14 is positioned in the region of the vessel to be treated, but also to ensure that the entire region of the vessel that is contacted by the inflated balloon 40 receives radiation treatment. This is necessary because, although balloon 40 is inflated to relatively low pressure, even the light engagement pressure between balloon 40 and the vessel being treated may be sufficient to stimulate hyperplasia. Accordingly, even where the target area 34 the vessel that requires IRT to prevent restenosis is shorter than the length of balloon 40, it is important that the region of the vessel corresponding to the entire length of balloon 40 be treated. Where radioguide catheter 10 is used in conjunction with an afterloader, (as described in the aforementioned application Ser. No. 08/057,332), the afterloader automatically steps or gradually moves the distal tip of a source wire between the markers 36 to achieve substantially uniform irradiation along the region of the vessel corresponding to the length of balloon 40. If, however, the catheter is used without an afterloader capable of multiple positioning of the radiation source, the radio opaque markers are essential for manual positioning of the radiation source or otherwise ensuring uniform dosage over the length of balloon 40.

Figure 3B:
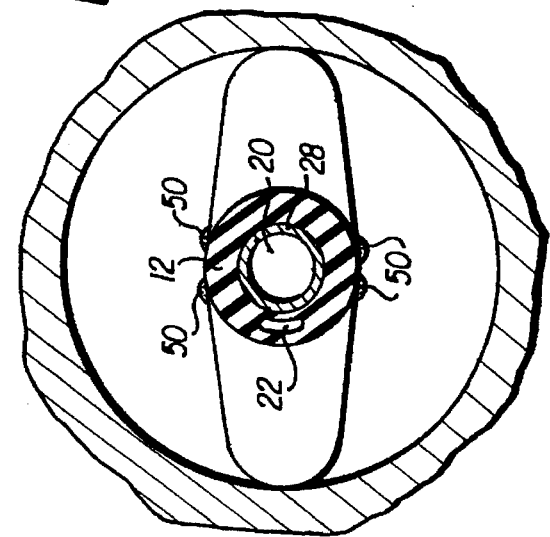
FIG. 3B is a transverse sectional view of an alternate embodiment of the present invention incorporating an over-the-wire guidewire lumen.

FIG. 3B is a transverse cross section of an alternate embodiment of the invention incorporating an over-the-wire guidewire lumen. In the over-the-wire configuration, guidewire lumen 26 runs substantially the length of shaft 12, rather than exiting distal of balloon 40 as does the distal monorail guidewire lumen 24 shown in FIG. 2. The presence of guidewire lumen 26 within the catheter shaft 12 in the treatment region introduces some eccentricity in the location of the treatment channel 20 within the shaft. In certain applications, this eccentricity will be within the centering tolerance and, therefore can be disregarded. Alternately the eccentricity can be compensated by incorporating an equal and opposite offset into the balloon design.

Figure 4:
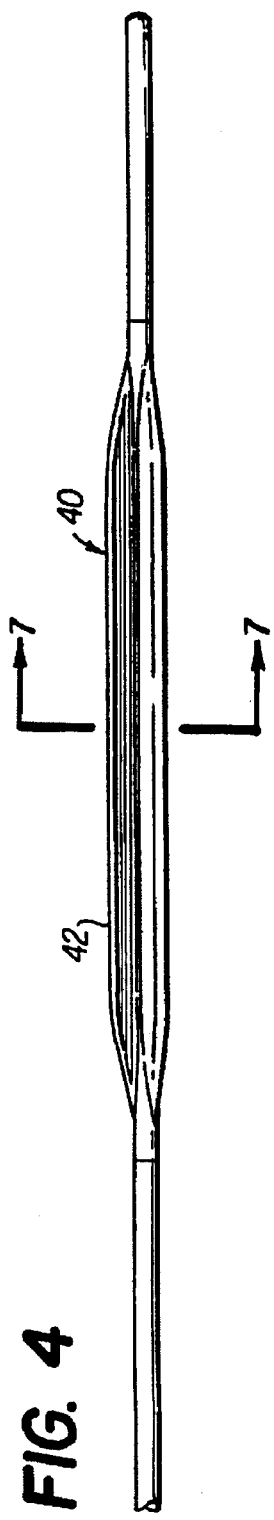
FIG. 4 is a plan view of an embodiment of the present invention incorporating a balloon with axial flutes.

FIG. 4 shows an alternate embodiment of the invention in which balloon 40 has longitudinal flutes 42 molded into its exterior surface. When engaged with the walls of the blood vessel, the flutes define straight longitudinal paths for perfusion of blood past treatment section 14. The flutes 42 can be molded with either equal or unequal radial length. Equal length flutes, as shown in FIG. 4 would center the catheter shaft exactly. Providing unequal radial lengths would provide the offset necessary to compensate for the eccentricity in the location of the treatment channel within the shaft in the embodiment of FIG. 3B.

Figure 5:
FIG. 5 is a plan view of an embodiment of the present invention incorporating segmented flutes.
Figure 6:
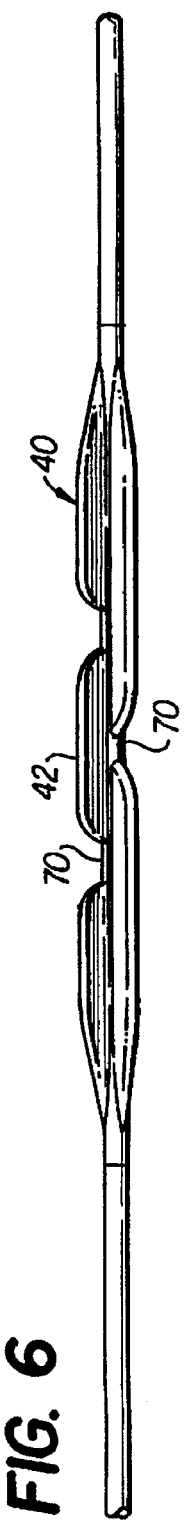
FIG. 6 is a plan view of an embodiment of the present invention incorporating staggered, segmented flutes

FIGS. 5–6 show alternate embodiments of the invention in which the balloon 40 has indentations 70 molded into flutes 42. When engaged with the walls of the blood vessel, the flutes define longitudinal and circumferential paths for perfusion of blood. Indentations 70 also add additional flexibility to flutes 42 to permit balloon 40 to be used in tortuous blood vessels without substantial loss of centering capability. Indentations 70 may be distributed uniformly along the axis of each flute as shown in FIG. 5, or each indentation 70 may be offset from the indentation 70 on each adjacent flute 40 to form a staggered series of circumferential perfusion paths as shown in FIG. 6.

Figure 7:
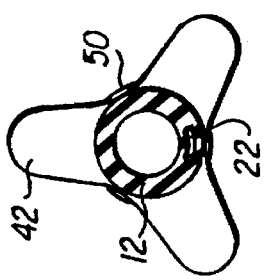
FIG. 7 is are enlarged transverse cross section of the embodiments of FIGS. 4–6 incorporating a distal monorail guidewire lumen.

FIG. 7 is a cross section taken at line 7—7, of the embodiments of FIGS. 4–6.

Figure 8A:
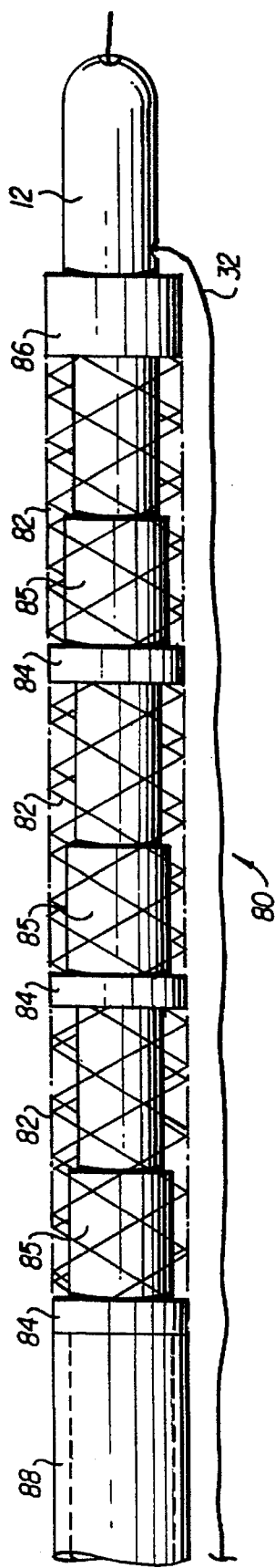
FIG. 8A and B are plan views of an embodiment of the present invention incorporating wire form centering means in their contracted and expanded states respectively.
Figure 8B:
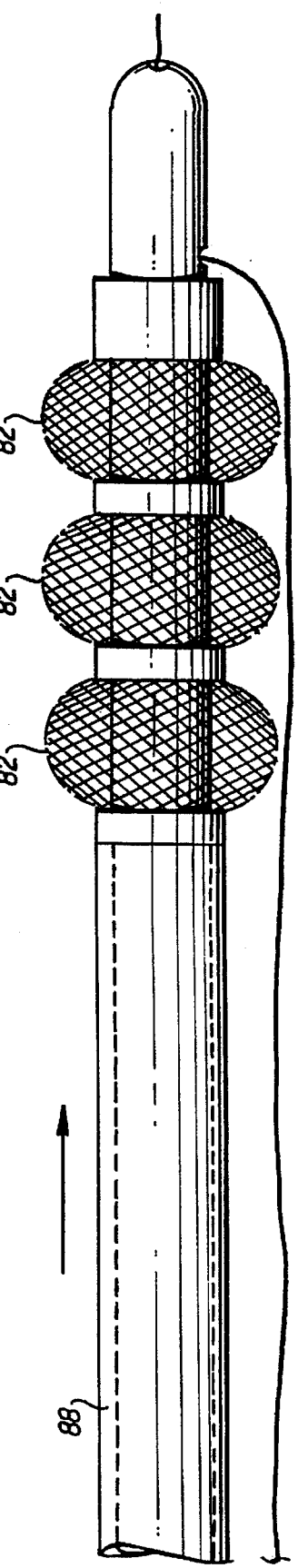

FIG. 8A and 8B show a plan view of an alternate embodiment employing wire forms 80 in lieu of balloon 40 to position the shaft 12 in the center of the blood vessel 30. Wire forms 80 comprise a series of wire mesh tubes 82 connected by a series of slidable collars 84 of slightly larger inside diameter than the outside diameter of shaft 12. Collars 84 may incorporate undercut regions 85 that act as spacers to limit the travel of the collars 84 along shaft 12. Wire mesh tubes 82 may be composed of the nickel titanium alloy known as Nitinol or other material having a high degree of deformability. End collar 86 is fixed near the distal end of shaft 12 proximal of guidewire exit 62. Expansion sheath 88 is a slidable sheath of slightly larger inside diameter than the outside diameter of shaft 12 and is attached to the proximal slidable collar 84. Activation of wire form 80 is effected by moving expansion sheath 88 distally, which compresses wire mesh tubes 82, forcing them outward as shown in FIG. 8B until the undercut regions 85 of the slidable collars 84 engage the proximal end of next adjacent collar, to stop the compression at a predetermined amount. Alternately, wire mesh tubes 82 may be pre-deformed so as to expand and engage the blood vessel in their relaxed state. Expansion sheath 88 would be kept in tension to contract the wire forms until the catheter is properly positioned.

Figure 9:
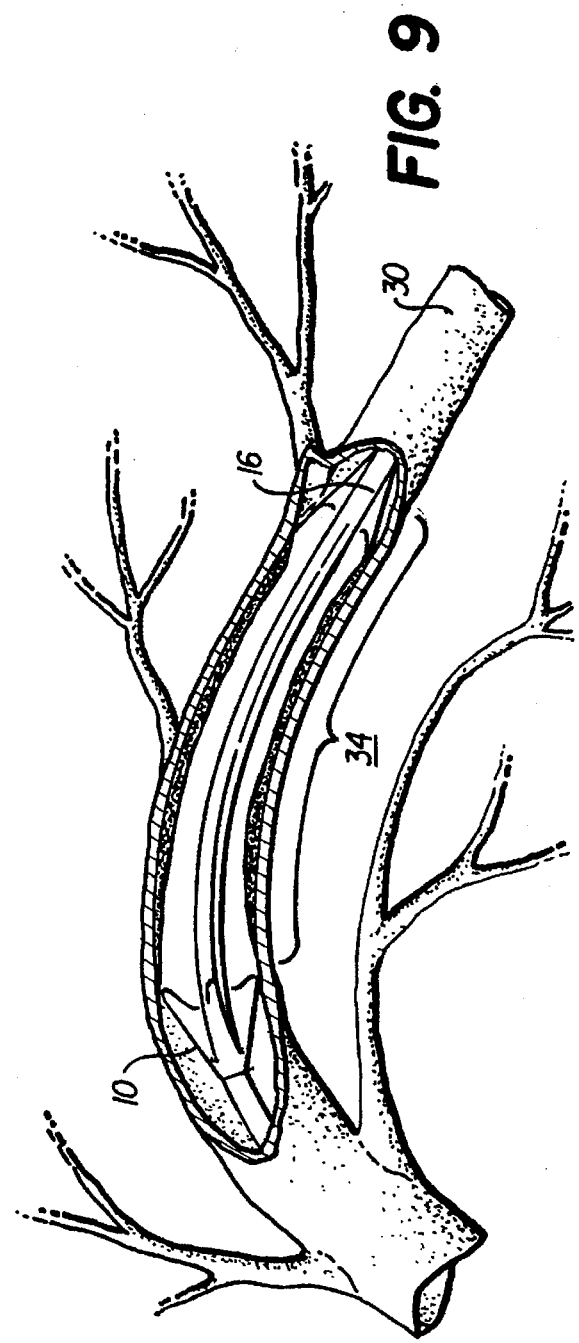
FIG. 9 is a perspective view of a blood vessel partially cut away to show an embodiment of the present invention.

FIG. 9 is a partial cut-away view of blood vessel 30, which may, for example, be a human coronary artery. With reference to FIGS. 1 and 9, after the PTCA or other unblocking procedure is completed, the physician performing the IRT procedure will select the appropriate catheter based on the nominal diameter achieved in the lumen opening procedure and based on the length of the traumatized section of the vessel. The physician will match as closely as possible the resultant diameter to the diameters available in his or her selection of catheters and will match the treatment length (distance between markers 36) so that it is at least approximately 1 millimeter longer than the traumatized area. The excess length provides tolerance to ensure that the entire target area receives the appropriate radiation treatment. The radiation dose will be calculated based on the nominal diameter of the deployed balloon (balloon radius being equal to the distance to target) and the radioactive source activity for that day to yield a treatment time. With balloon 40 in a collapsed state, the distal tip 16 of radioguide catheter 10 is implanted in the patient and guided through the cardiovascular system via fluoroscopy until the treatment section 14 is centered in the target area 34 as indicated by reference to radio-opaque markers 36. The proximal end of radioguide catheter 10 may be connected to an afterloader via an afterloader connector (as described in the aforementioned application Ser. No. 08/057,332) or other device for advancing a source wire through treatment channel 20 to the target area 34. Once the catheter 10 is in position, balloon 40 is inflated via inflation lumen 22 until the lobes 38 of balloon 40 engage the interior wall of blood vessel 30. With balloon 40 inflated to center treatment channel 20, the afterloader advances the source wire along treatment channel 20 until the radioactive source of the source wire is disposed in treatment section 14 of catheter 10. The source wire is positioned for the treatment interval calculated to achieve the desired dose of radiation, which, depending on the isotope is typically from about 4–8 minutes or up to 30 minutes for very low activity sources. After the appropriate treatment interval, the source wire is withdrawn. Balloon 40 is then deflated and catheter 10 withdrawn from the patient.

By maintaining the radioactive source substantially at the center of the lumen, the present invention assures a sufficient dosage of radiation is received over the entire traumatized area, yet eliminates the potentially serious side effects of overexposure caused by uncontrolled radial placement of the radioactive source within the vessel. Thus, the present invention makes IRT a safer and more effective treatment for prevention of stenosis and restenosis.

Although certain preferred embodiments and methods have been disclosed herein, it will be apparent from the foregoing disclosure to those skilled in the art that variations and modifications of such embodiments and methods may be made without departing from the true spirit and scope of the invention. Accordingly, it is intended that the invention shall be limited only to the extent required by the appended claims and the rules and principles of applicable law.

What is claimed is:

1. An apparatus for localized intravascular radiotherapy of a tortuous blood vessel, such as a coronary artery, comprising:

a catheter comprising an elongate member having a proximal section and a distal section, the distal section including a distal tip, said catheter being sized and of sufficient flexibility for introduction into a lumen of a patient's vascular system and advancement therethrough until the distal tip is disposed near a predetermined target area of tissue along the wall of the tortuous blood vessel, said elongate member having a longitudinal bore, the longitudinal bore having an opening in the proximal section and terminating proximate to the distal tip to form a treatment channel within said catheter for advancement of a radioactive source wire therein; and means for substantially centering the treatment channel radially within the lumen of the tortuous blood vessel over a predetermined length of treatment channel despite curvature of the blood vessel, in at least said predetermined target area;

whereby a radioactive source wire, including a distal end having a radioactive source assembled thereto, when advanced along the treatment channel until the radioactive source is disposed at the target area, will have said radioactive source maintained substantially at the radial center of the lumen throughout the target area for delivery of a substantially uniform dosage of radiation to tissue at the wall of the blood vessel in the target area circumferentially about said source throughout a predetermined treatment interval.

2. An apparatus for localized intravascular radiotherapy of a tortuous blood vessel, such as a coronary artery, comprising:

a catheter comprising an elongate member having a proximal section and a distal section, the distal section including a distal tip, said catheter being sized and of sufficient flexibility for introduction into a lumen of a patient's vascular system and advancement therethrough until the distal tip is disposed near a predetermined target area of tissue along the wall of the tortuous blood vessel, said elongate member having a longitudinal bore, the longitudinal bore having an opening in the proximal section and terminating proximate to the distal tip to form a treatment channel within said catheter for advancement of a radioactive source wire therein; and means for substantially centering the treatment channel radially within the lumen of the tortuous blood vessel in at least said predetermined target area;

whereby a radioactive source wire, including a distal end having a radioactive source assembled thereto, when advanced along the treatment channel until the radioactive source is disposed at the target area, will have said radioactive source maintained substantially at the radial center of the lumen at the target area for delivery of a substantially uniform dosage of radiation to tissue at the wall of the blood vessel in the target area circumferentially about said source;

said centering means comprising a wire form, said wire form comprising at least one wire mesh tube having a proximal end and a distal end slidably assembled over said elongate member;

the distal end of said at least one wire mesh tube being attached to said elongate member proximate to the distal end thereof;

further including a sleeve comprising a hollow, flexible, elongate tube having a proximal end and a distal end, said sleeve being slidably assembled over said elongate member, the proximal end of said wire mesh tube being attached to the distal end of said sleeve;

whereby said at least one wire mesh tube is expanded radially to compliantly engage the interior surface of the blood vessel by exertion of an axial force along said sleeve to axially compress said wire mesh tube.

3. The apparatus of claim 1 wherein said centering means comprises a balloon positioned and adapted to be inflated to compliantly engage the interior surface along a portion of the wall of the tortuous blood vessel.

4. The apparatus of claim 3 wherein said balloon includes a distal end and a proximal end, said balloon being attached to said catheter at the proximal and distal ends of said balloon and at a location between the distal and proximal ends of said balloon to leave portions of the balloon unattached to the catheter between the proximal and distal ends thereof.

5. The apparatus of claim 3 wherein the balloon includes means for allowing perfusion of blood through the region of the blood vessel along said portion of the wall while the balloon is inflated.

6. The apparatus of claim 5 wherein said perfusion means comprises a balloon lobe defining a helical passage between said balloon and the interior surface along a portion of the wall of the blood vessel when the balloon is inflated to engage said interior surface.

7. The apparatus of claim 5 wherein said perfusion means comprises a plurality of longitudinal balloon flutes defining substantially straight axial passages between said balloon and the interior surface along a portion of the wall of the tortuous blood vessel when the balloon is inflated to engage said interior surface.

8. The apparatus of claim 7 wherein the number of flutes is from 3 to 7.

9. The apparatus of claim 8 wherein said flutes further include indentations that define a circumferential passage between said balloon and the interior surface along a portion of the wall of the blood vessel when the balloon is inflated to engage said interior surface.

10. The apparatus of claim 9 wherein the indentations are staggered axially to define a staggered circumferential passage.

11. An apparatus for localized intravascular radiotherapy of a tortuous blood vessel, such as a coronary artery, comprising:

a catheter comprising an elongate member having a proximal section and a distal section, the distal section including a distal tip, said catheter being sized and of sufficient flexibility for introduction into a lumen of a patient's vascular system and advancement therethrough until the distal tip is disposed near a predetermined target area of tissue along the wall of the tortuous blood vessel, said elongate member having a longitudinal bore, the longitudinal bore having an opening in the proximal section and terminating proximate to the distal tip to form a treatment channel within said catheter for advancement of a radioactive source wire therein; and means for substantially centering the treatment channel radially within the lumen of the tortuous blood vessel in at least said predetermined target area, said centering means comprising a balloon positioned and adapted to be inflated to compliantly engage the interior surface along a portion of the wall of the tortuous blood vessel, said balloon including a distal end and a proximal end, said balloon being attached to said catheter at the proximal and distal ends of said balloon and at a location between the distal and proximal ends of said balloon to leave portions of the balloon unattached to the catheter between the proximal and distal ends thereof;

whereby a radioactive source wire, including a distal end having a radioactive source assembled thereto, when advanced along the treatment channel until the radioactive source is disposed at the target area, will have said radioactive source maintained substantially at the radial center of the lumen at the target area for delivery of a substantially uniform dosage of radiation to tissue at the wall of the blood vessel in the target area circumferentially about said source;

further including radio-opaque markers fixed to said catheter proximate to each of the distal end and the proximal end of the balloon to facilitate fluoroscopic observation of positioning of the balloon in the target area for irradiation of a region of the blood vessel corresponding to the length of the balloon engaging the interior surface of the blood vessel.

12. An apparatus for localized intravascular radiotherapy of a tortuous blood vessel, such as a coronary artery, comprising:

a catheter comprising an elongate member having a proximal section and a distal section, the distal section including a distal tip, said catheter being sized and of sufficient flexibility for introduction into a lumen of a patient's vascular system and advancement therethrough until the distal tip is disposed near a predetermined target area of tissue along the wall of the tortuous blood vessel, said elongate member having a longitudinal bore, the longitudinal bore having an opening in the proximal section and terminating proximate to the distal tip to form a treatment channel within said catheter for advancement of a radioactive source wire therein, the proximal section of said elongate member of the catheter further including an afterloader connector; and means for substantially centering the treatment channel radially within the lumen of the tortuous blood vessel in at least said predetermined target area;

whereby a radioactive source wire, including a distal end having a radioactive source assembled thereto, when advanced along the treatment channel until the radioactive source is disposed at the target area, will have said radioactive source maintained substantially at the radial center of the lumen at the target area for delivery of a substantially uniform dosage of radiation to tissue at the wall of the blood vessel in the target area circumferentially about said source.

13. An apparatus for localized intravascular radiotherapy of a tortuous blood vessel, such as a coronary artery, comprising:

a catheter comprising an elongate member having a proximal section and a distal section, the distal section including a distal tip, said catheter being sized and of sufficient flexibility for introduction into a lumen of a patient's vascular system and advancement therethrough until the distal tip is disposed near a predetermined target area of tissue along the wall of the tortuous blood vessel, said elongate member having a longitudinal bore, the longitudinal bore having an opening in the proximal section and terminating proximate to the distal tip to form a treatment channel within said catheter for advancement of a radioactive source wire therein; and means for substantially centering the treatment channel radially within the lumen of the tortuous blood vessel in at least said predetermined target area;

whereby a radioactive source wire, including a distal end having a radioactive source assembled thereto, when advanced along the treatment channel until the radioactive source is disposed at the target area, will have said radioactive source maintained substantially at the radial center of the lumen at the target area for delivery of a substantially uniform dosage of radiation to tissue at the wall of the blood vessel in the target area circumferentially about said source;

further including an over-the-wire guidewire lumen, said over-the-wire guidewire lumen comprising a first longitudinal hole in said elongate member, said first longitudinal hole having an opening in the proximal section and an opening at the distal tip of said elongate member.

14. An apparatus for localized intravascular radiotherapy of a tortuous blood vessel, such as a coronary artery, comprising:

a catheter comprising an elongate member having a proximal section and a distal section, the distal section including a distal tip, said catheter being sized and of sufficient flexibility for introduction into a lumen of a patient's vascular system and advancement therethrough until the distal tip is disposed near a predetermined target area of tissue along the wall of the tortuous blood vessel, said elongate member having a longitudinal bore, the longitudinal bore having an opening in the proximal section and terminating proximate to the distal tip to form a treatment channel within said catheter for advancement of a radioactive source wire therein; and means for substantially centering the treatment channel radially within the lumen of the tortuous blood vessel in at least said predetermined target area, said centering means comprising a balloon positioned and adapted to be inflated to compliantly engage the interior surface along a portion of the wall of the tortuous blood vessel;

whereby a radioactive source wire, including a distal end having a radioactive source assembled thereto, when advanced along the treatment channel until the radioactive source is disposed at the target area, will have said radioactive source maintained substantially at the radial center of the lumen at the target area for delivery of a substantially uniform dosage of radiation to tissue at the wall of the blood vessel in the target area circumferentially about said source;

further including an over-the-wire guidewire lumen, said over-the-wire guidewire lumen comprising a first longitudinal hole in said elongate member, said first longitudinal hole having an opening in the proximal section and an opening at the distal tip of said elongate member.

15. The apparatus of claim 14 further including a balloon inflation lumen, said balloon inflation lumen comprising a second longitudinal hole in said elongate member, said second longitudinal hole having an opening in the proximal section and an opening inside the balloon.

16. An apparatus for localized intravascular radiotherapy of a tortuous blood vessel, such as a coronary artery, comprising:

a catheter comprising an elongate member having a proximal section and a distal section, the distal section including a distal tip, said catheter being sized and of sufficient flexibility for introduction into a lumen of a patient's vascular system and advancement therethrough until the distal tip is disposed near a predetermined target area of tissue along the wall of the tortuous blood vessel, said elongate member having a longitudinal bore, the longitudinal bore having an opening in the proximal section and terminating proximate to the distal tip to form a treatment channel within said catheter for advancement of a radioactive source wire therein; and means for substantially centering the treatment channel radially within the lumen of the tortuous blood vessel in at least said predetermined target area;

whereby a radioactive source wire, including a distal end having a radioactive source assembled thereto, when advanced along the treatment channel until the radioactive source is disposed at the target area, will have said radioactive source maintained substantially at the radial center of the lumen at the target area for delivery of a substantially uniform dosage of radiation to tissue at the wall of the blood vessel in the target area circumferentially about said source;

further including a distal monorail guidewire lumen, said lumen comprising a second longitudinal bore and a transverse opening;

said second longitudinal bore extending from the distal tip of said elongate member to a point proximate to the distal end of the treatment channel; and said transverse opening comprising a hole intersecting said second longitudinal bore and opening to a lateral surface of said elongate member.

17. An apparatus for localized intravascular radiotherapy of a tortuous blood vessel such as a coronary artery, comprising:

a catheter comprising an elongate member having a proximal section and a distal section, the distal section including a distal tip, said catheter being sized and of sufficient flexibility for introduction into a lumen of a patient's vascular system and advancement therethrough until the distal tip is disposed near a predetermined target area of tissue along the wall of the tortuous blood vessel said elongate member having a longitudinal bore, the longitudinal bore having an opening in the proximal section and terminating proximate to the distal tip to form a treatment channel within said catheter for advancement of a radioactive source wire therein; and means for substantially centering the treatment channel radially within the lumen of the tortuous blood vessel in at least said predetermined target area, said centering means comprising a balloon positioned and adapted to be inflated to compliantly engage the interior surface along a portion of the wall of the tortuous blood vessel;

whereby a radioactive source wire, including a distal end having a radioactive source assembled thereto, when advanced along the treatment channel until the radioactive source is disposed at the target area, will have said radioactive source maintained substantially at the radial center of the lumen at the target area for delivery of a substantially uniform dosage of radiation to tissue at the wall of the blood vessel in the target area circumferentially about said source;

further including a distal monorail guidewire lumen, said distal monorail guidewire lumen comprising a second longitudinal bore extending from the distal tip of said elongate member to a point proximate to the distal end of the treatment channel and a transverse opening comprising a hole intersecting said second longitudinal bore and opening to a lateral surface of said elongate member.

18. The apparatus of claim 17 further including a balloon inflation lumen, said balloon inflation lumen comprising a longitudinal hole in said elongate member, said longitudinal hole having an opening in the proximal section and an opening inside the balloon.

19. A method of intravascular radiotherapy treatment of a predetermined target area of tissue along a portion of the wall of a tortuous blood vessel, such as a coronary artery, comprising:

introducing into the vascular system of a patient an elongate flexible member having a proximal end and a distal end and a longitudinal bore, and having a length and a diameter adapted to permit said member to traverse a tortuous path through a lumen of the patient's vascular system to said target area, said member further including means for centering said distal end radially in the lumen of the blood vessel over a predetermined length at said distal end substantially equivalent to the entire length of lumen of the target area despite curvature thereof attributable to the tortuosity of the blood vessel;

advancing said member until the distal end is disposed within the target area of the blood vessel;

radially centering the longitudinal bore along the entire length of lumen of the target area of the blood vessel by compliantly engaging the centering means with the wall of the blood vessel;

advancing a source wire including a distal tip having a radioactive source assembled thereto along the longitudinal bore until the radioactive source is disposed within the lumen at the target area of the blood vessel;

substantially centering the radioactive source radially in the lumen along the target area over a predetermined period of treatment time to deliver a substantially uniform dosage of radiation to tissue in a circumferential band about said source sufficient to inhibit hyperplasia of smooth muscle cells in the irradiated tissue; and withdrawing the source wire from the patient's vascular system upon completion of the predetermined period of treatment time.

20. The method of claim 19 wherein centering of the radioactive source is accomplished to within about 0.5–0.7 millimeters of the true radial center of the blood vessel along the entire length of the target area.

21. The method of claim 19 wherein radial centering of the radioactive source is controlled over the length of the target area so as to limit the dosage of radiation to tissue in said circumferential band to an amount in a range from about 1,000 to about 3,000 rads throughout the target area.

22. The method of claim 19 further including:

irradiating substantially uniformly said tissue in the target area along a region of the blood vessel corresponding to the length of the centering means engaging the interior surface of the blood vessel.

23. A method of inhibiting restenosis of a selected portion of a human coronary artery after angioplasty or other trauma to said selected portion, comprising:

selecting a catheter comprising an elongate flexible member having a proximal section and a distal section, the distal section including a distal tip, said catheter further including a longitudinal bore having an opening in the proximal section and terminating proximate to the distal tip to form a treatment channel within said catheter, said treatment channel having a proximal portion and a distal portion, the distal section of said catheter further including means for substantially centering a length of the distal portion of the treatment channel substantially corresponding to the length of said selected portion of the artery radially within the lumen of the coronary artery despite curvature of the artery;

introducing and advancing said catheter within the cardiovascular system of a patient to place the distal section of said catheter in proximity to said selected portion in the lumen of the coronary artery;

engaging the centering means with the wall of the coronary artery to substantially center said distal portion length of the treatment channel radially in the lumen of the artery throughout the length of said selected portion thereof despite any said curvature of the artery over said length of the selected portion;

advancing a source wire having a distal end along the treatment channel until a radioactive source assembled at said distal end of the source wire is disposed substantially at the radial center of the lumen of the coronary artery within said selected portion thereof, maintaining the radioactive source substantially at the radial center of the lumen of the coronary artery in advancement of the source along the length of said selected portion throughout a predetermined treatment period to deliver a substantially uniform dosage of radiation to tissue in a circumferential band about said radioactive source at the wall of the coronary artery in said selected portion thereof; and withdrawing the source wire from the patient upon completion of the treatment period.

24. The method of claim 23 wherein the selecting is made from an array of catheters having centering means adapted to engage various lengths and diameters of selected portion of coronary arteries.

* * * * *